United States Patent
Hulse et al.

(10) Patent No.: US 9,126,888 B2
(45) Date of Patent: *Sep. 8, 2015

(54) AZEOTROPE-LIKE COMPOSITIONS OF TETRAFLUOROPROPENE AND WATER

(71) Applicant: HONEYWELL INTERNATIONAL INC., Morristown, NJ (US)

(72) Inventors: Ryan Hulse, Getzville, NY (US); Haluk Kopkalli, Staten Island, NY (US); Hang T. Pham, Amherst, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/299,172

(22) Filed: Jun. 9, 2014

(65) Prior Publication Data

US 2014/0284517 A1   Sep. 25, 2014

Related U.S. Application Data

(63) Continuation of application No. 13/082,980, filed on Apr. 8, 2011, now Pat. No. 8,747,691.

(51) Int. Cl.
| | |
|---|---|
| *C09K 5/04* | (2006.01) |
| *C07C 21/18* | (2006.01) |
| *C07C 17/38* | (2006.01) |
| *C07C 17/383* | (2006.01) |
| *C07C 17/386* | (2006.01) |
| *C07C 17/389* | (2006.01) |

(52) U.S. Cl.
CPC ............... *C07C 21/18* (2013.01); *C07C 17/38* (2013.01); *C07C 17/383* (2013.01); *C07C 17/386* (2013.01); *C07C 17/389* (2013.01)

(58) Field of Classification Search
CPC .......................................................... C09K 5/04
USPC ................. 252/67, 182.15; 570/180; 514/772
See application file for complete search history.

(56) References Cited

U.S. PATENT DOCUMENTS

| | | | | |
|---|---|---|---|---|
| 7,279,451 | B2 * | 10/2007 | Singh et al. | 510/412 |
| 8,065,882 | B2 * | 11/2011 | Singh et al. | 62/6 |
| 8,148,317 | B2 * | 4/2012 | Singh et al. | 510/408 |
| 8,444,874 | B2 * | 5/2013 | Singh et al. | 252/68 |
| 8,518,293 | B2 * | 8/2013 | Hulse et al. | 252/67 |
| 8,623,808 | B2 * | 1/2014 | Singh et al. | 510/408 |
| 8,741,829 | B2 * | 6/2014 | Singh et al. | 510/408 |
| 8,747,691 | B2 * | 6/2014 | Hulse et al. | 252/67 |
| 2006/0043331 | A1 * | 3/2006 | Shankland et al. | 252/67 |
| 2007/0007488 | A1 * | 1/2007 | Singh et al. | 252/68 |
| 2009/0278076 | A1 * | 11/2009 | Singh et al. | 252/68 |
| 2009/0285764 | A1 * | 11/2009 | Singh et al. | 424/45 |
| 2009/0302285 | A1 * | 12/2009 | Singh et al. | 252/602 |
| 2009/0305876 | A1 * | 12/2009 | Singh et al. | 502/150 |
| 2013/0247597 | A1 * | 9/2013 | Kontomaris | 62/77 |

* cited by examiner

*Primary Examiner* — Douglas McGinty
(74) *Attorney, Agent, or Firm* — Bruce Bradford

(57) ABSTRACT

Provided are azeotropic and azeotrope-like compositions of trans-1,3,3,3-tetrafluoropropene (HFO-1234ze(E)) and water. Such azeotropic and azeotrope-like compositions are useful in isolating trans-1,3,3,3-tetrafluoropropene from impurities during production. Azeotropes of the instant invention are similarly useful in final compositions or for the manufacture of final compositions, such as blowing agent, propellants, refrigerants, diluents for gaseous sterilization and the like.

18 Claims, No Drawings

AZEOTROPE-LIKE COMPOSITIONS OF TETRAFLUOROPROPENE AND WATER

CROSS-REFERENCE TO RELATED APPLICATIONS

This application is a continuation of U.S. application Ser. No. 13/082,980, filed Apr. 8, 2011, now U.S. Pat. No. 8,747,691, which application claims the priority benefit of U.S. Provisional Application No. 61/331,980, filed May 6, 2010, the contents of which are incorporated herein by reference.

FIELD OF THE INVENTION

The present invention pertains to azeotropic and azeotrope-like compositions of trans-1,3,3,3-tetrafluoropropene (HFO-1234ze(E)) and water.

BACKGROUND OF THE INVENTION

Traditionally, chlorofluorocarbons (CFCs) like trichlorofluoromethane and dichlorodifluoromethane have been used as refrigerants, blowing agents and diluents for gaseous sterilization. In recent years, there has been universal concern that completely halogenated chlorofluorocarbons might be detrimental to the Earth's ozone layer. Therefore, stratospherically safer alternatives to these materials are desirable.

There is presently a worldwide effort to use fluorine-substituted hydrocarbons which contain fewer or no chlorine substituents. The production of HFCs, i.e. compounds containing only carbon, hydrogen and fluorine, has been the subject of interest to provide environmentally desirable products that could provide a substitute to CFCs. Such compounds are known in the art to be produced by reacting hydrogen fluoride with various hydrochlorocarbon compounds. While HFCs are considered to be much more environmentally advantageous than hydrochlorofluorocarbons (HCFCs) or chlorofluorocarbons (CFCs) because they are not non-ozone depleting, recent data indicates that they may also contribute to greenhouse global warming. Accordingly, alternatives to HFCs, HCFCs, and CFCs are also being explored.

Hydrofluoroolefins ("HFOs") have been proposed as possible replacements. It is generally known that HFOs are best used as a single component fluid or azeotropic mixture, neither of which fractionate upon boiling and evaporation. The identification of such compositions is difficult due, at least in part, to the relative unpredictability of azeotrope formation. Therefore, industry is continually seeking new HFO-based mixtures that are acceptable and environmentally safer substitutes for CFCs, HCFCs, and HFCs. This invention satisfies these needs among others.

SUMMARY OF THE INVENTION

The present invention relates to an azeotropic or azeotrope-like composition of trans-1,3,3,3-tetrafluoropropene (HFO-1234ze(E)) and water. The compositions of the instant invention provide environmentally desirable replacements for currently used CFCs, HFCs and HCFCs, since HFO-1234ze(E) and water have little to no ozone depletion potential. Additionally, a composition containing such an azeotrope exhibits characteristics that make it better than CFCs, HFCs, and HCFCs substitutes, as well as either HFO-1234ze(E) or water alone.

In one aspect, the present invention provides a composition and method of forming an azeotropic or azeotrope-like composition which comprises a blend of from about 0.1 to about 50 weight percent water and about 50 to about 99.9 weight percent HFO-1234ze(E). In certain embodiments, azeotropic or azeotrope-like composition comprises a blend of from about 0.1 to about 30 weight percent water and about 70 to about 99.9 weight percent HFO-1234ze(E), and, in further embodiments, about 1 to about 27 weight percent water and about 73 to about 99 weight percent HFO-1234ze(E). Azeotrope or azeotrope like compositions of the present invention the exhibit a boiling point of about −19° C.±0.5° C. at a pressure of about 14.3 psia±2 psia. In further embodiments, the azeotrope has a boiling point of about −19° C. at a pressure of about 14.3 psia, and in even further embodiments, the azeotrope has a boiling point of about −19.3° C. at a pressure of about 14.3 psia.

Further embodiments of the present invention relate to methods for removing trans-1,3,3,3-tetrafluoropropene from a mixture containing trans-1,3,3,3-tetrafluoropropene and at least one impurity by adding water to the mixture in an effective amount to form an azeotropic or azeotrope-like composition in accordance with the foregoing. This azeotrope is then separated from impurities using standard methods known in the art, such as but not limited to, distillation. Impurities may include one or more halocarbons and/or hydrogen fluoride, which may or may not be miscible with trans-1,3,3,3-tetrafluoropropene. Examples of halocarbons include, but are not limited to, 1,1,1,3,3-pentafluoropropane and cis-1,3,3,3-tetrafluoropropene. In further embodiments, the impurities may or may not also form an azeotropic mixture with trans-1,3,3,3-tetrafluoropropene, water or a mixture of trans-1,3,3,3-tetrafluoropropene and water.

Further embodiments of the present invention relate to methods for isolating trans-1,3,3,3-tetrafluoropropene from an azeotropic mixture of trans-1,3,3,3-tetrafluoropropene and water by separating trans-1,3,3,3-tetrafluoropropene from the water. Separation methods may include any one or combination of methods known in the art or otherwise discussed herein. For example, trans-1,3,3,3-tetrafluoropropene may be separated using a liquid-liquid phase separation. In alternative embodiments, trans-1,3,3,3-tetrafluoropropene may be separated using distillation and/or one or more drying media (e.g. a molecular sieve, silica alumina or the like). In further embodiments, separation methods may include a combination of liquid-liquid phase separation and a second method selected from distillation and/or one or more drying media.

Additional embodiments and advantages of the instant invention will be apparent to one of ordinary skill in the art, based on the disclosure provided herein.

DETAILED DESCRIPTION OF THE INVENTION

In one aspect of the present invention, an azeotropic or azeotrope-like composition is provided of trans-1,3,3,3-tetrafluoropropene (HFO-1234ze(E)) and water. This composition provides environmentally desirable replacements for currently used CFCs, HFCs, and HCFCs, since HFO-1234ze(E) and water have little to no ozone depletion potential. Additionally, a composition containing such an azeotrope exhibits characteristics that make it better than CFC, HFC, and HCFC substitutes, as well as HFO-1234ze(E) or water alone. In a further aspect of the instant invention, the azeotrope or azeotrope-like composition of HFO-1234ze(E) and water is used to isolate a purified form of HFO-1234ze(E).

Azeotrope or azeotrope-like mixtures of HFO-1234ze(E) and water, include those compositions or mixtures that behave like azeotropes. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

Accordingly, the invention provides azeotrope-like compositions effective amounts of HFO-1234ze(E) and water. As used herein, "effective amounts" means an amount of each component that, on combination with the other component, results in the formation of an azeotrope-like composition. In certain embodiments, the azeotropic mixture contains from about 0.1 to about 50 percent water and about 50 to about 99.9 percent HFO-1234ze(E) based on the weight of the azeotropic or azeotrope-like composition. In further embodiments, the azeotropic or azeotrope-like composition contains a blend of from about 0.1 to about 30 weight percent water and about 70 to about 99.9 weight percent HFO-1234ze(E), and, in even further embodiments, about 1 to about 27 weight percent water and about 73 to about 99 weight percent HFO-1234ze (E). The azeotropic mixture of the present invention has a boiling point of about −19° C.±0.5° C. at a pressure of about 14.3±2 psia. In further embodiments, azeotropic mixture of the present invention has a boiling point of about −19° C. at a pressure of about 14.3 psia. In an even further embodiment, the azeotrope has a boiling point of from about −19.3° C. at a pressure of from about 14.3 psia.

In one embodiment, the methods of the present invention include the steps for generating the HFO-1234ze(E) and HFO-1234ze(E)/water azeotrope and for isolating the azeotrope from impurities. The instant methods also include steps for purifying HFO-1234ze(E) from the azeotropic mixture, which are discussed in greater detail below. HFO-1234ze(E) may be generated using any method known in the art. In one non-limiting example, HFO-1234ze(E) is formed from the dehydrohalogenation of precursor haloalkane reagents, resulting in a mixture of HFO-1234ze(E) and one or more impurities. US patent application 20080051611, the contents of which are incorporated herein by reference, outlines one embodiment of such a process in which 1,1,1,3,3-pentafluoropropane (HFC-245fa) is dehydrohalogenated in the presence of HF to form a mixture of HFO-1234ze(E), cis-1,3,3,3-tetrafluoropropene (HFO-1234ze(Z)), HFC-245fa and hydrogen fluoride (HF). The first step in removing HFO-1234ze(E) from this mixture, or any similar mixture containing HFO-1234ze(E) and an impurity, is by adding water in an effective amount to form an azeotropic composition of the HFO-1234ze(E) and water. Thereafter, the azeotropic composition is separated from the impurity using standard separation techniques, such as, but not limited to, distillation, scrubbing, or other art recognized separating means. In one embodiment, the impurity itself does not form an azeotropic mixture with HFO-1234ze(E), water or a mixture of HFO-1234ze(E) and water. In another embodiment, the impurity does form an azeotropic mixture with HFO-1234ze(E), water or a mixture of HFO-1234ze(E) and water. Typical impurities of HFO-1234ze(E) include, but are not limited to, other halocarbons which may be miscible with HFO-1234ze(E) such as, but not limited to, 1,1,1,3,3-pentafluoropropane (HFC-245fa) and/or cis-1,3,3,3-tetrafluoropropene (HFO-1234ze(Z)). In further embodiments, the impurity is hydrogen fluoride (HF) alone or in combination with any of the foregoing.

This purified azeotrope meets the need in the art for HFO mixtures that have no ozone depletion potential and are negligible contributors to greenhouse global warming and are nonflammable. Such a mixture may be utilized within a composition or in the manufacture of a composition having a wide range of uses such as, but not limited, refrigerants, blowing agents, propellants and diluents for gaseous sterilization. The azeotrope may be provided in combination with other useful additives or ingredients for such purposes.

In further embodiments, it also may be desirable to separate component parts of the HFO-1234ze(E) and water azeotrope to a purified form HFO-1234ze(E). Separation methods may include any method generally known in the art. In one embodiment, for example, the excess water can be removed from the HFO-1234ze(E) by liquid-liquid phase separation. The remaining water can then be removed from the HFO-1234ze(E) by distillation and/or a drying media (e.g. molecular sieves silica alumina, and the like). Purified HFO-1234ze (E) may be used as an end product (i.e. as a refrigerant, blowing agent, propellant, diluents for gaseous sterilization, or the like), or it may be further processed for the production of alternative HFOs or similar compounds.

The following non-limiting examples serve to illustrate the invention.

EXAMPLES

Example 1

A glass vacuum insulated vessel fitted with a dry ice cooled condenser is initially charged with 1234ze(E). Water is then added incrementally and the temperature of the mixture is recorded. The temperature of the mixture reaches a minimum values and then flattens indicating the formation of a heterogeneous azeotrope. The ambient pressure during the measurements was 14.3 psia. The measured temperatures are shown in Table 1.

TABLE 1

Ebulliometer measurements of HFO-1234ze(E) and water at 14.3 psi

| water, wt % | Temp, ° C. |
|---|---|
| 0.00 | −19.33 |
| 1.52 | −19.34 |
| 2.12 | −19.35 |
| 4.44 | −19.35 |
| 6.66 | −19.34 |
| 10.79 | −19.35 |
| 14.58 | −19.34 |
| 18.06 | −19.34 |
| 21.26 | −19.34 |
| 24.23 | −19.34 |
| 26.98 | −19.34 |

We claim:

1. A blowing agent composition comprising an azeotropic or azeotrope-like composition consisting essentially of from about 73 to 98.48 weight percent trans-1,3,3,3-tetrafluoropropene (HFO-1234ze(E)) and from 1.52 to about 27 weight percent water.

2. The blowing agent composition of claim 1, wherein the azeotrope or azeotrope-like composition consists of water and trans-1,3,3,3-tetrafluoropropene.

3. The blowing agent composition of claim 1, wherein water is provided in an amount from 2.12 to about 27 weight percent and HFO-1234ze(E) is provided in an amount from about 73 to 97.88 weight percent 4. The blowing agent composition of claim 1, wherein the azeotrope or azeotrope-like composition has a boiling point of about −19° C. ±0.5° C. at a pressure of about 14.3 psia±2psia.

5. The blowing agent composition of claim 1, wherein the azeotrope or azeotrope-like composition has a boiling point of about −19.3° C. at a pressure of about 14.3 psia.

6. The blowing agent composition of claim 1, wherein the azeotrope or azeotrope-like composition has a boiling point of about −19° C. at a pressure of about 14.3 psia.

7. A refrigerant composition comprising an azeotropic or azeotrope-like composition consisting essentially of from about 73 to 98.48 weight percent trans-1,3,3,3-tetrafluoropropene (HFO-1234ze(E)) and from 1.52 to about 27 weight percent water.

8. The refrigerant composition of claim 7, wherein the azeotrope or azeotrope-like composition consists of water and trans-1,3,3,3-tetrafluoropropene.

9. The refrigerant composition of claim 7, wherein water is provided in an amount from 2.12 to about 27 weight percent and HFO-1234ze(E) is provided in an amount from about 73 to 97.88 weight percent.

10. The refrigerant composition of claim 7, wherein the azeotrope or azeotrope-like composition has a boiling point of about −19° C. ±0.5° C. at a pressure of about 14.3 psia±2 psia.

11. The refrigerant composition of claim 7, wherein the azeotrope or azeotrope-like composition has a boiling point of about −19.3° C. at a pressure of about 14.3 psia.

12. The refrigerant composition of claim 7, wherein the azeotrope or azeotrope-like composition has a boiling point of about −19° C. at a pressure of about 14.3 psia.

13. A propellant composition comprising an azeotropic or azeotrope-like composition consisting essentially of from about 73 to 98.48 weight percent trans-1,3,3,3-tetrafluoropropene (HFO-234ze(E)) and from 1.52 to about 27 weight percent water.

14. The propellant composition of claim 13, wherein the azeotrope or azeotrope-like composition consists of water and trans-1,3,3,3-tetrafluoropropene.

15. The propellant composition of claim 13, wherein water is provided in an amount from 2.12 to about 27 weight percent and HFO-1234ze(E) is provided in an amount from about 73 to 97.88 weight percent 16. The propellant composition of claim 13, wherein the azeotrope or azeotrope-like composition has a boiling point of about −19° C. ±0.5° C. at a pressure of about 14.3 psia±2 psia.

17. The propellant composition of claim 13, wherein the azeotrope or azeotrope-like composition has a boiling point of about −19.3° C. at a pressure of about 14.3 psia.

18. The propellant composition of claim 13, wherein the azeotrope or azeotrope-like composition has a boiling point of about −19° C. at a pressure of about 14.3 psia.

* * * * *